United States Patent [19]

Tsuchiya et al.

[11] Patent Number: 4,966,915

[45] Date of Patent: Oct. 30, 1990

[54] L-DOPA DERIVATIVES OR THEIR ACID ADDITION SALTS, PROCESS FOR PRODUCING SAME AND THEIR USE

[75] Inventors: Yoshimi Tsuchiya, Funabashi; Masahiro Hayashi, Ichikawa; Hiroshi Takehana, Tokyo; Akihiro Hisaka, Ichikawa; Yoshio Sawasaki, Tokyo; Masaki Ihara, Kawasaki, all of Japan

[73] Assignee: Banyu Pharmaceutical Co., Ltd., Tokyo, Japan

[21] Appl. No.: 245,348

[22] Filed: Sep. 16, 1988

[30] Foreign Application Priority Data

Sep. 18, 1987 [JP] Japan ............................ 62-234299
Feb. 13, 1988 [JP] Japan ............................ 63-31260

[51] Int. Cl.$^5$ .................. C07C 69/00; A61K 31/215
[52] U.S. Cl. ............................ 514/531; 260/404; 514/512; 514/529; 514/530; 514/544; 514/532; 514/546; 514/549; 514/552; 558/271; 560/1; 560/55; 560/65; 560/73; 560/105; 560/109; 560/122; 560/123; 560/124; 560/125; 560/126; 560/142
[58] Field of Search .................. 560/142, 55, 65, 73, 560/105, 109, 122, 123, 124, 125, 1, 126; 558/271; 260/410.5, 404; 514/512, 529, 530, 531, 532, 544, 546, 549, 552

[56] References Cited

U.S. PATENT DOCUMENTS

| | | | |
|---|---|---|---|
| 2,868,818 | 1/1959 | Pfister | 560/40 |
| 3,725,470 | 4/1973 | Bretschneider | 560/142 |
| 3,859,331 | 1/1975 | Kaiser | 560/40 |
| 3,891,696 | 6/1975 | Bodor | 560/40 |
| 3,983,138 | 9/1976 | Saari | 560/142 |
| 4,311,706 | 1/1982 | Bodor | 560/142 |

OTHER PUBLICATIONS

Roche, "Design of Biopharmaceutical Properties through Prodrugs and Analogs".

Primary Examiner—Michael L. Shippen
Attorney, Agent, or Firm—Sherman and Shalloway

[57] ABSTRACT

An L-dopa derivative represented by formula (I)

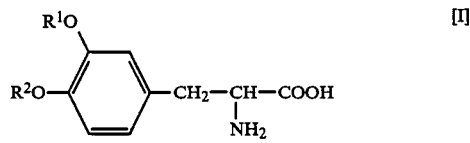

wherein one of $R^1$ and $R^2$ denotes a hydrogen atom and the other denotes a group of formula R—CO— in which R denotes an alkyl, alkenyl, optionally substituted cycloalkyl, optionally substituted phenyl, optionally substituted aralkyl, lower alkoxy or optionally substituted aralkyloxy group, and its acid addition salt. The compounds are useful in the medical field, especially in the treatment of a series of diseases called Parkinson's disease or Parkinsonism.

25 Claims, 5 Drawing Sheets

L-DOPA DERIVATIVES OR THEIR ACID ADDITION SALTS, PROCESS FOR PRODUCING SAME AND THEIR USE

This invention relates to novel L-dopa derivatives, and more specifically, to novel L-dopa derivatives or their acid addition salts useful in the medical field, especially in the treatment of a series of diseases called Parkinson's disease or Parkinsonism, a process for producing same and their use.

L-Dopa has been developed as a precursor of dopamine to make up for deficiency in dopamine in the brain of patients with Parkinson's disease, and is now generally accepted as the first drug of choice in the field. Long-term therapy with L-dopa is, however, associated with a variety of problems, such as motor fluctuations, short duration of action, loss of drug responsiveness, etc. The diskinesia and end-of-dose deterioration ("wearing off") are probably the most common motor fluctuations seen in Parkinson's disease patients treated chronically with L-dopa. The dyskinesias mean abnormal involuntary movements such as chorea and athetosis observed in jaws, limbs, neck, etc, which often appear 1-2 hours after administration of L-dopa. These dyskinesias correlate with dose and blood concentration of L-dopa, so they are well managed by reducing the size of each individual dose or increasing frequency of dosing. The end-of-dose deterioration means repeating motor fluctuation with short period of relief and aggravation of the disease, which are parallel to the blood level of L-dopa. Smaller, more frequent doses of L-dopa usually improve patients experiencing end-of-dose deterioration. The other problems, such as short duration of action or another kind of the drug-induced motor fluctuations, are indicated to attribute to a rapid elimination of L-dopa from blood (refer to Eur. J. Clin. Pharmacol., vol. 25, p. 69, 1983 and Experientia, vol 40, p. 1165, 1984). In order to solve the above problems, it is vital to suppress a rapid increase in blood level of L-dopa and attain a longlasting blood level of L-dopa with less fluctuation (see Neurology, vol. 34, p. 1131, 1984 & vol. 36, p. 739, 1986 and N. Eng. J. Med., vol. 30, p. 484, 1984).

When L-dopa itself is administered to the patients, the blood level of L-dopa rapidly increases and falls; it is therefore difficult to cope with the foregoing problems. For this reason, L-dopa is often administered up to 7 times a day or intravenously injected continually. These treatments, however, are indeed a great burden on the patients.

A number of attempts have been hitherto made to produce various L-dopa derivatives, especially to make prodrugs of L-dopa on the premise that they are converted to L-dopa in vivo. However, there is no clinically used L-dopa prodrug which has been successfully designed to accomplish a long-lasting blood level and durable efficacy of L-dopa [see J. Med. Chem., vol. 20, p. 1435, 1977, ibid., vol. 29, p. 687, 1986, Eur. J. Med. Chem., vol. 20, p. 459, 1985, Japanese Laid-open Patent Applications No. 9567/1972 (British Patent No. 1347375), No. 31949/1972 & No. 72150/1973 (British Patent No. 1378419) and U.S. Pat. No. 3,939,253].

It is an object of this invention to solve the problems in L-dopa therapy by suppressing adverse effects caused by the rapid and excessive increase in blood level of L-dopa when administering L-dopa, maintaining a clinically effective blood level of L-dopa for a long period of time and attaining a favorable pharmacokinetic profile of L-dopa with less fluctuation.

In order to solve the foregoing problems, the present inventors have made extensive studies to prepare prodrugs of L-dopa, and consequently discovered that a monoester of L-dopa catechol represented by formula I) below does not cause a rapid and excessive increase in blood level of L-dopa on oral administration, maintains a clinically effective blood level of L-dopa for a long period of time and gives a favorable pharmacokinetic profile of L-dopa with less fluctuation. Said discovery has led to completion of this invention.

Namely, this invention is to provide a novel L-dopa derivative represented by formula I

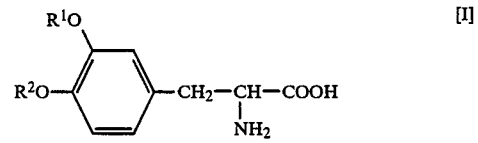

wherein one of $R^1$ and $R^2$ denotes a hydrogen atom and the other denotes a group of formula R—CO— in which R denotes an alkyl, alkenyl, optionally substituted cycloalkyl, optionally substituted phenyl, optionally substituted aralkyl, lower alkoxy or optionally substituted aralkyloxy group,
and its acid addition salt, a process for producing same and its use in the treatment of Parkinson's disease.

Various terms used in the specification and appended claims and suitable examples thereof are explained hereinafter.

The "alkyl group" can be linear or branched, and examples thereof are $C_1$–$C_{19}$ alkyl groups such as methyl, ethyl, propyl, isopropyl, butyl, isobutyl, sec-butyl, tert-butyl, pentyl, isopentyl, sec-pentyl, tert-pentyl, neopentyl, hexyl, isohexyl, heptyl, octyl, nonyl, decyl, undecyl, dodecyl, tridecyl, tetradecyl, pentadecyl, hexadecyl, heptadecyl, octadecyl, nonadecyl and 2,4,4-trimethylpentyl groups. Among these groups, $C_3$–$C_5$ alkyl groups such as the isopropyl, sec-butyl, tert-butyl, isopentyl, sec-pentyl, tert-pentyl and neopentyl groups are especially preferable as the branched alkyl groups; meanwhile $C_4$–$C_{15}$, above all, $C_7$–$C_{13}$ alkyl groups such as heptyl, octyl, nonyl, decyl, undecyl, dodecyl and tridecyl groups are especially preferable as the linear alkyl groups.

The "alkenyl group" may also be branched, and examples thereof are $C_2$–$C_{19}$ alkenyl groups such as vinyl, 1-propenyl, 2-propenyl, 1,3-butadienyl, 8-heptadecenyl, 8,11-heptadecadienyl, 8,11,14-heptadecatrienyl and 4,7,10,13-nonadecatetraenyl groups.

Examples of the "optionally substituted cycloalkyl group" are $C_3$–$C_7$ cycloalkyl groups such as cyclopropyl, cyclobutyl, cyclopentyl, cyclohexyl and cycloheptyl groups. These cycloalkyl groups may have one or two substituents selected from $C_1$–$C_4$ alkyl groups, $C_1$–$C_4$ alkoxy groups and halogen atoms. Concrete examples of the thus substituted cycloalkyl groups are 1-methylcyclopropyl, 2,2-dimethylcyclopropyl, 1-methylcyclobutyl, 2,2-dimethylcyclobutyl, 1-methylcyclopentyl, 2,2-dimethylcyclopentyl, 1-methylcyclohexyl, 2,2-dimethylcyclohexyl, 1-methylcycloheptyl and 2,2-dimethylcycloheptyl groups. Thus, preferable examples of the "optionally substituted cycloalkyl group" in this invention are $C_3$–$C_6$ cycloalkyl groups which may be substituted by one or two alkyl groups, especially, $C_3$–$C_6$ cycloalkyl groups which may be substituted by one $C_1$–$C_4$ alkyl group such as a cyclopropyl, 1-methylcyclopropyl, cyclopentyl, 1-methylcyclopentyl, cyclohexyl or 1-methylcyclohexyl group.

In the "optionally substituted phenyl group", one or two substituents selected from $C_1$–$C_4$ alkyl groups, $C_1$–$C_4$ alkoxy groups and halogen atoms can be present on the benzene ring. Examples of such optionally substituted phenyl group are phenyl, 4-methylphenyl, 4-methoxyphenyl, 3,4-dimethoxyphenyl, 4-chlorophenyl and 4-fluorophenyl groups. Among these groups, the phenyl group is especially preferable.

In the "optionally substituted aralkyl group", typically, the optionally substituted phenyl moiety includes the optionally substituted phenyl-alkyl group having the above meaning. Examples thereof are $C_7$–$C_{12}$ aralkyl groups such as benzyl, 4-methylbenzyl, 4-methoxybenzyl, 3,4-dimethoxybenzyl, 4-chlorobenzyl, phenethyl and alpha-methylbenzyl groups. Among these groups, the benzyl group is especially preferable.

The "lower alkoxy group" may be either linear or branched, and examples thereof are $C_1$–$C_6$ alkoxy groups such as methoxy, ethoxy, propoxy, isopropoxy, butoxy, isobutoxy, sec-butoxy, tert-butoxy, penthyloxy and hexyloxy groups.

The optionally substituted aralkyl moiety of the "optionally substituted aralkyloxy group" has the above meaning, and examples thereof are $C_7$–$C_{12}$ aralkyloxy groups such as benzyloxy, 4-methylbenzyloxy, 2-methoxybenzyloxy, 2-chlorobenzyloxy, 4-methoxybenzyloxy, 4-chlorobenzyloxy, phenetyloxy and alpha-methylbenzyloxy groups.

Examples of the "halogen atom" are fluorine, chlorine, bromine and iodine.

In the above formula I, only one of $R^1$ and $R^2$ is an acyl group (R—CO—) and the other is a hydrogen atom. In this invention, a compound of formula [I] wherein $R^1$ is a hydrogen atom and $R^2$ is an acyl group (R—CO—), i.e. a compound of formula [I-a]

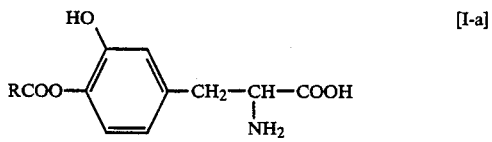

wherein R is as defined above, is preferable.

Preferable examples of the compound of formula [I] provided by this invention include compounds of formula [I] wherein R is a branched $C_3$–$C_5$ alkyl, a linear $C_4$–$C_{15}$ alkyl group or a $C_3$–$C_6$ cycloalkyl group which may be substituted by one or two $C_1$–$C_4$ alkyl groups. Above all, compounds of formula [I] wherein R is a branched $C_3$–$C_5$ alkyl group or a $C_3$–$C_6$ cycloalkyl group which may be substituted by one $C_1$–$C_4$ alkyl group are preferable.

More preferable compounds are compounds of formula [I] wherein R is a tert-butyl group, a cyclopropyl group or a 1-methylcyclopropyl group.

The compound of formula [I] can be present in the form of an acid addition salt based on the amino group present. Examples of such acid addition salt are salts of inorganic acids such as hydrochloric acid, hydrobromic acid, hydriodic acid, sulfuric acid, nitric acid, perchloric acid and phosphoric acid; and salts of organic acids such as p-toluenesulfonic acid, benzenesulfonic acid, methanesulfonic acid and trifluoroacetic acid. Pharmaceutically acceptable acid addition salts are especially preferable.

The compound of formula [I] and its salt provided by this invention can be produced by reacting L-dopa that may be protected with an acylating agent represented by formula [II]

wherein Q denotes a leaving group and R is as defined above,
then removing the protecting group present, and if required, converting the resulting L-dopa derivative of formula [I] into its acid addition salt.

The "L-dopa that may be protected" here referred to means L-dopa represented by formula [III]

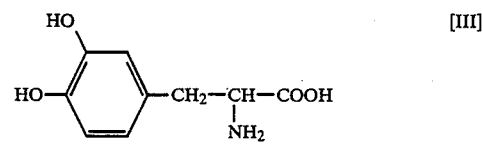

wherein a carboxyl group, an amino group and/or one of the two hydroxyl groups (i.e. the hydroxyl group of which acylation is not desired) present on the catechol moiety, being reactive functional groups of L-dopa, may be protected by a protecting group known per se in the field of a peptide chemistry. Thus, Examples of the protecting group of the amino group are benzyl, benzyloxycarbonyl, tert-butoxycarbonyl and p-nitrobenzyloxycarbonyl groups. Examples of the protecting group of the carboxyl group are benzyl, benzhydryl, p-nitrobenzyl, tert-butyl and allyl groups. Examples of the protecting group of the hydroxyl group are benzyl, methoxymethyl, benzyloxycarbonyl, tert-butyldimethylsilyl groups.

The above protecting groups can be introduced in L-dopa of formula III by a usual method in the field of the peptide chemistry.

However, the reaction between L-dopa of formula [III] and the acylating agent of formula [II] fully proceeds by selecting the amount of the acylating agent and the other reaction conditions without protecting the reactive functional groups of L-dopa. Accordingly, from the economical aspect of the procedure, it is convenient to use L-dopa in unprotected form.

On the other hand, the leaving group (Q) in the acylating agent of formula [II] can be an acid residue of a carboxylic acid ester-forming reactive derivative such as a halide or an acid anhydride. Examples thereof are halogen atoms such as chlorine, bromine and iodine; and acyloxy groups such as ethoxycarbonyloxy, acetoxy, propionyloxy, isopropionyloxy, butyryloxy, isobutyryloxy, pivaloyloxy, cyclopropanecarbonoyloxy and 2-methylcyclopropancarbonoyloxy groups.

The reaction between L-dopa which may be protected and the acylating agent of formula II) can be performed, for example, at a reaction temperature of about $-20°$ C. to about $100°$ C., preferably about $-10°$ C. to about $70°$ C. in such a solvent as not to adversely affect the reaction, for example, dioxane, tetrahydrofuran, ethyl acetate, acetonitrile, dimethylformamide, benzene, toluene, ethyl ether, chloroform, methylene chloride, trifluoroacetic acid, or a mixture thereof. Though the reaction is influenced by the type of the acylating agent, the reaction temperature and the type of the solvent, it is usually finished in 30 minutes to 48 hours.

The amount of the acylating agent of formula [II] varies depending on whether or not L-dopa as a starting material is protected, or the type of the acylating agent and the reaction conditions. Generally, it can be 0.8 to 10 mols per mol of L-dopa which may be protected.

Particularly, when L-dopa with two hydroxyl groups of the catechol moiety unprotected (the carboxyl group and/or amino group of L-dopa may be protected) is used as a starting material, it is advisable that the amount of the acylating agent of formula [II] is about 0.9 to about 1.1 mols per mol of said L-dopa in order to suppress diacylation of the catechol moiety, and it is preferable to use said acylating agent in a substantially equimolar amount.

When L-dopa with the amino group unprotected (the carboxyl group and/or one hydroxyl group may be protected), above all, the unprotected L-dopa, is used as a starting material, it is convenient to conduct the acylation reaction in the presence of at least 1 mol, preferably 1.1 to 10 mols of an acid per mol of said L-dopa. Examples of the acid are inorganic acids such as hydrochloric acid, hydrobromic acid, hydriodic acid, sulfuric acid, nitric acid, perchloric acid and phosphoric acid; and organic acids such as p-toluenesulfonic acid, benzenesulfonic acid, methanesulfonic acid and trifluoroacetic acid.

On the other hand, when L-dopa with the amino group protected is used as a starting material, it is advisable to perform the acylation reaction in the presence of a base. Examples of the base are inorganic bases such as sodium hydroxide, potassium hydroxide, sodium carbonate and sodium bicarbonate; and organic bases such as triethylamine and pyridine. The amount of the base is not particularly limited. Generally, about 1 to 2 mols per mol of said L-dopa is suitable.

As an embodiment of a method for adding the starting material to the reaction system, there is used a method in which a base or an acid is added, if required, to a solution obtained by dissolving or suspending L-dopa which may be protected in the above solvent, and the acylating agent is added dropwise over a period of 10 minutes to 1 hour with stirring. If it is necessary to prepare the acylating agent in advance, a method is available wherein the solution or suspension of L-dopa which may be protected is added dropwise to the acylating agent prepared in advance.

In case the protecting group is present in the final compound of formula [I] in this invention obtained by the foregoing process, said protecting group can be removed by a known method suitable for said protecting group. For example, when the carboxyl group, the amino group or one hydroxyl group of the catechol moiety in L-dopa is protected with a benzyl, benzyloxycarbonyl or nitrobenzyl group, the protecting group can be removed by catalytic reduction in the presence of a hydrogenation catalyst such as palladium-carbon. When the reactive functional group of L-dopa is protected with a tert-butyl group, a methoxymethyl group, a tert-butoxycarbonyl group, a tert-butyldimethylsilyl group, etc., it can be removed by the treatment with an acid such as hydrochloric acid, trifluoroacetic acid, etc. in a solvent such as water, tetrahydrofuran, ethyl acetate, anisole, etc.

The final compound of formula [I] in this invention formed by the above process can be isolated from the reaction mixture and purified by a method known per se. For instance, an organic solvent such as ethyl ether, petroleum ether, hexane or isopropyl ether is added to the reaction mixture to precipitate crystals. After the crystals are collected by filtration, recrystallization is conducted with water, methanol, ethanol, propanol, isopropanol, tetrahydrofuran, acetone, ethyl ether or a mixture thereof. Alternatively, when the product is an acid addition salt, the crystals are dissolved or suspended in water, and pH is adjusted to 5 to 6 by a base such as sodium hydroxide or potassium hydroxide. The crystals are collected by filtration and if required, recrystallized with a water-isopropanol solvent. Or to the reaction mixture is added ethyl ether, petroleum ether, hexane or isopropyl ether to provide a precipitate. After the precipitate is dissolved in water, the solution is put on a column of a nonpolar adsoption resin such as Diaion HP-20 R (a tradename for a product made by Mitsubishi Chemical Industries, Ltd.) or Amberlite XAD R (a tradename for a product made by Amberlite), and then the eluate is concentrated to give a product which is subsequently purified by recrystallization. By the way, the above methods can be properly combined if required.

The thus obtained L-dopa derivative of formula [I] can be converted into its acid addition salt, if required, by treating it with the aforesaid inorganic acid or organic acid.

L-Dopa used as a starting material in producing the compound of this invention can easily be obtained by a method described in e.g. Chem. Pharm. Bull., vol. 10, p.657, 1962, Helv. Chim. Acta, vol. 56, p. 1708, 1970 and Japanese Laid-open Patent Application No. 9576/1972 (British Patent No. 1347375).

The compound of formula [I] in this invention which is obtained by the above method, i.e. the L-dopa mono O-acyl product is usually present as a single 3-O-acyl product or 4-O-acyl product in crystalline state. However, in the solution, the acyl group is easy to migrate between hydroxyl groups at the 3- and 4-positions, so that it is sometimes present as a mixture of 3- and 4-O-isomers.

The L-dopa mono O-acyl product or its acid addition salt of this invention has an excellent activity against Parkinson's disease and is useful as a treating agent of Parkinson's disease. When the L-dopa mono O-acyl product in this invention is used as said treating agent, said compound is formulated into a usual pharmaceutical preparation containing it together with the organic or inorganic carrier or diluent, which is suited for oral or parenteral administration. Said pharmaceutical preparation can be administered either orally or parenterally. The pharmaceutical preparation may contain an ordinary organic or inorganic nontoxic inactive carrier or diluent such as gelatin, lactose, sucrose, titanium oxide, starch, crystalline cellulose, hydroxypropylmethyl cellulose, carboxymethyl cellulose, corn starch, microcrystalline wax, white soft paraffine, magnesium meta-silicic acid aluminate, anhydrous sodium phosphate, anhydrous calcium phosphate, hydroxypropyl cellulose, sorbitol, sorbitan fatty acid ester, polyvinyl pyrrolidone, magnesium stearate, light anhydrous silicic acid, talc, vegetable oil, benzyl alcohol, gum arabic, propylene glycol or polyalkylene glycol. The pharmaceutical preparation can take a common solid administration form such as a tablet with or without sugar coating, suppository or capsule, or a common liquid administration form such as a solution, suspension or emulsion. Pharmaceutical compositions can be subjected to ordinary pharmaceutical treatment, e.g. sterilization and/or contain antiseptics, stabilizers, wetting agents, emulsifying agents, salts to adjust an osmotic pressure and buffering agents.

The preparation is produced to contain 1 to 99% by weight, preferably about 25 to about 95% by weight of the active ingredient of formula [I] and 1 to 99% by weight, preferably about 5 to about 75% by weight of the inactive carrier or diluent.

The preperation can further contain other substances useful for medical treatment. Examples thereof are L-aromatic amino acid decarboxylase inhibitors having an activity to suppress peripheral decarboxylation of L-dopa, such as (−)-L-alpha-hydrazino-3,4-dihydroxyalpha-methylhydrocinnamic acid (generic name: carbidopa) and DL-serine-2-(2,3,4-trihydroxyphenyl)methyl)hydrazide (generic name: benserazide). These L-aromatic amino acid decarboxylase inhibitors can be contained in a proportion of generally 1 to 1/15 mol, preferably 1/2 to 1/10 mol per mol of the L-dopa derivative of formula [I] or its acid.

When the L-dopa mono-O-acyl product in this invention is used as a treating agent of Parkinson's disease, the dose and the flucuency of administration vary with the degree of symptoms, the age and weight of patients and if used with other medicines, the type of medicines. Usually, in the oral administration, it is advisable that the medicine is administered to an adult patient at a dose of 0.5 to 50 mg/kg a day at a time or in several divided portions.

Test Examples of the compound in this invention are described hereinafter to concretely make clear its availability.

The drawings quoted in Test Examples below are explained hereinafter.

Drugs used in Test Examples below have the following meanings.

Compound A: 4-O-pivaloyl-L-dopa
Compound B: 4-O-(1-methylcyclopropanecarbonyl)-L-dopa

TEST EXAMPLE 1

Measuring blood levels of L-dopa after oral administration of drugs (rats)

Seven to eight week-old SD-strain male rats (n=4) were previously fasted for 18 hours. A preparation (a preparation obtained by dissolving or suspending 20 mg of L-dopa as a control drug or the equimolar amount of each of the test drugs together with 4 mg of carbidopa in 20 ml of water containing 0.5% sodium carboxymethylcellulose and 0.1% Tween 80) was orally administered to the rats at a dose of 10 mg/kg (10 mg eq./kg, calculated as L-dopa). Immediately after administration, or 15, 30, 60, 90, 120, 150, 180, 240, 300 or 360 minutes after administration, 120 $\mu$l of blood was collected through a carotid cannula intubated in advance three days before the test, using a heparin-treated glass capillary. The blood was immediately subjected to centrifugal separation (3000 rpm, 10 minutes, 4° C.). To 40 $\mu$l of the resulting plasma was added 160 $\mu$l of a 0.5N perchloric acid aqueous solution containing 0.1% EDTA 2Na and 0.05% glutathione, and the mixture was centrifuged (10000 rpm, 10 minutes, 4° C.) to remove protein. The concentration of L-dopa in the resulting supernatant liquid was measured by a highperformance liquid chromatography (HPLC) with an electrochemical detector [column NUCLEOSIL $C_{18}$ (5 $\mu$m) 250 mm ×4.6 mm $\phi$, mobile phase: 0.1M citric acid/0.1M trisodium citrate=1/2 (containing 0.1 mM EDTA 2Na), flow rate: 0.8 ml/min, applied voltage: 600 mV].

Figure 1:
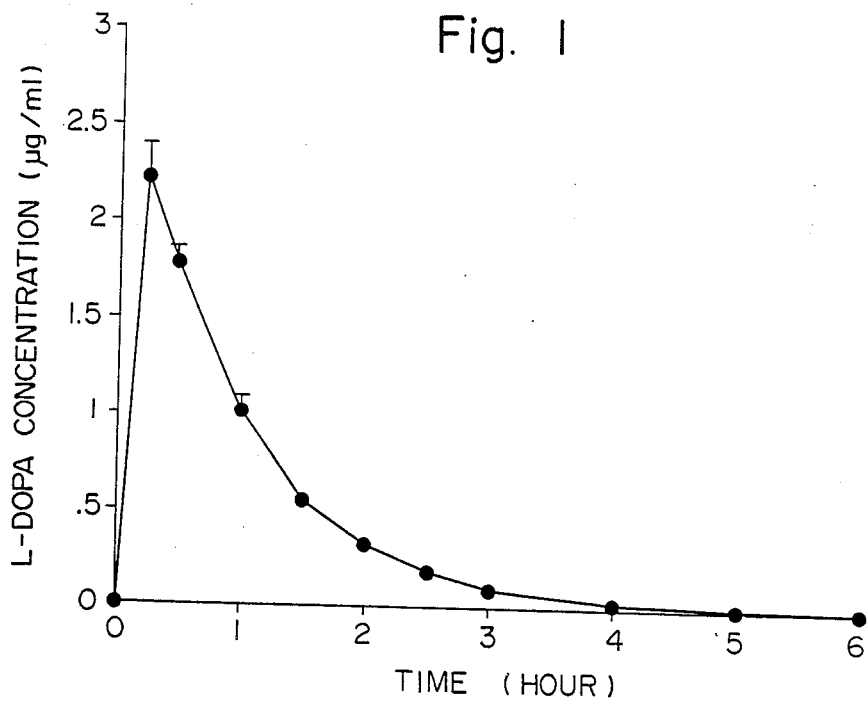
FIG. 1 illustrates change with time of a blood level of L-dopa in orally administering L-dopa to rats.
Figure 2:
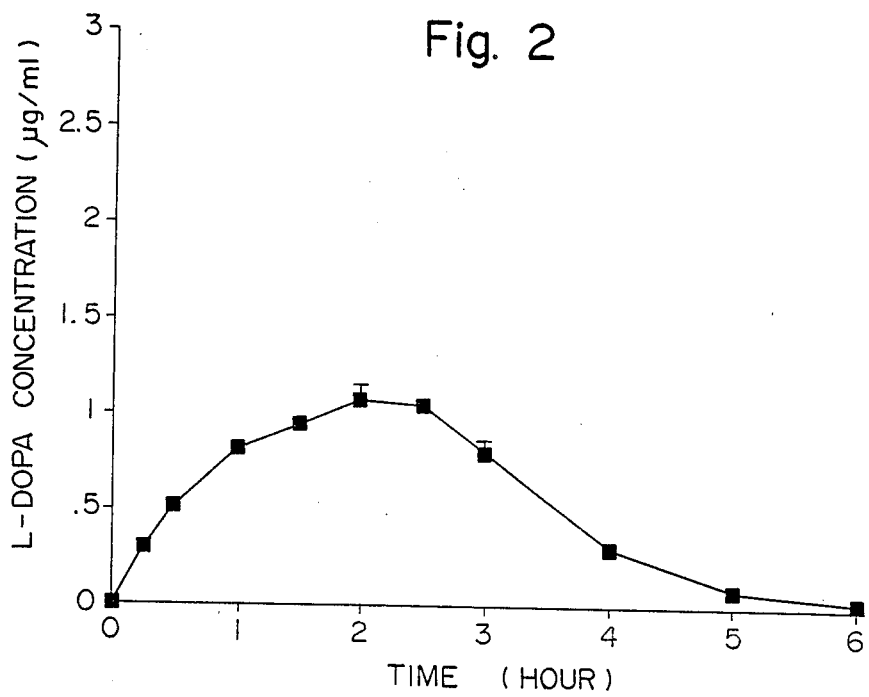
FIG. 2 illustrates change with time of a blood level of L-dopa in orally administering Compound A to rats.
Figure 3:
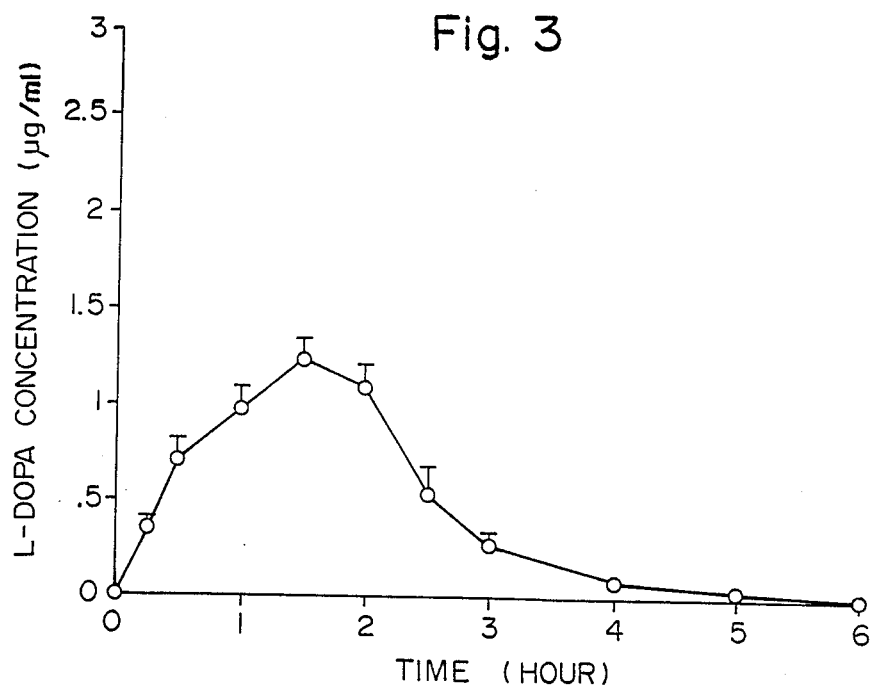
FIG. 3 illustrates change with time of a blood level of L-dopa in orally administering Compound B to rats.

The results are shown in FIGS. 1 to 3. In the blood level of L-dopa following oral administration of the test drugs, no rapid increase or elimination is observed and the duration time is markedly prolonged, showing a clinically favorable blood level profile, in comparison with L-dopa as the control drug. Moreover, in that case, an area under the blood curve (AUC) of the test drugs shows a higher value than that of L-dopa.

TEST EXAMPLE 2

Measuring blood levels of L-dopa after oral administration of drugs (dogs)

Beagle dogs (n=4) were previously fasted for 20 hours, and 0.05 mg/kg of haloperidol was intravenously injected therein 15 minutes before administering the drugs. A drug preparation obtained by suspending 1.00 g of L-dopa as a control drug or the equimolar amount of each of the test drugs together with 0.2 g of carbidopa in 200 ml of water containing 0.5% sodium carboxymethylcellulose and 0.1% Tween 80 was orally administered to the dogs at a dose of 2.0 ml/kg (10 mg eq./kg, calculated as L-dopa) via an oral catheter. Immediately after administration, or 15, 30, 60, 90, 120, 180, 240, 360 or 480 minutes after administration, 1 ml of blood was collected via the cephalic vein with a heparin-treated syringe. The blood was treated as in Test Example 1 and then measured for blood levels of L-dopa.

Figure 4:
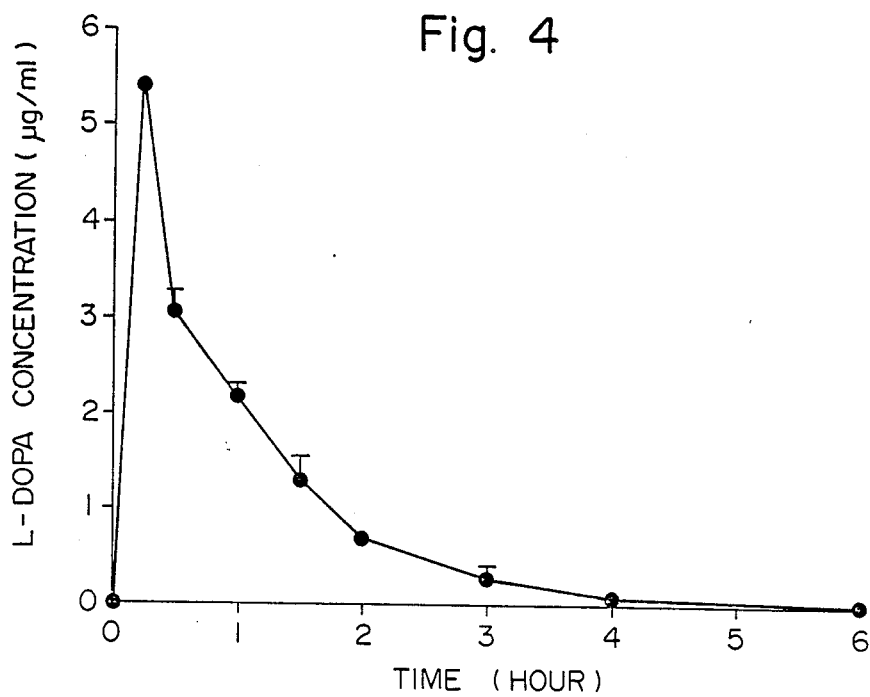
FIG. 4 illustrates change with time of a blood level of L-dopa in orally administering L-dopa to Beagle dogs.
Figure 5:
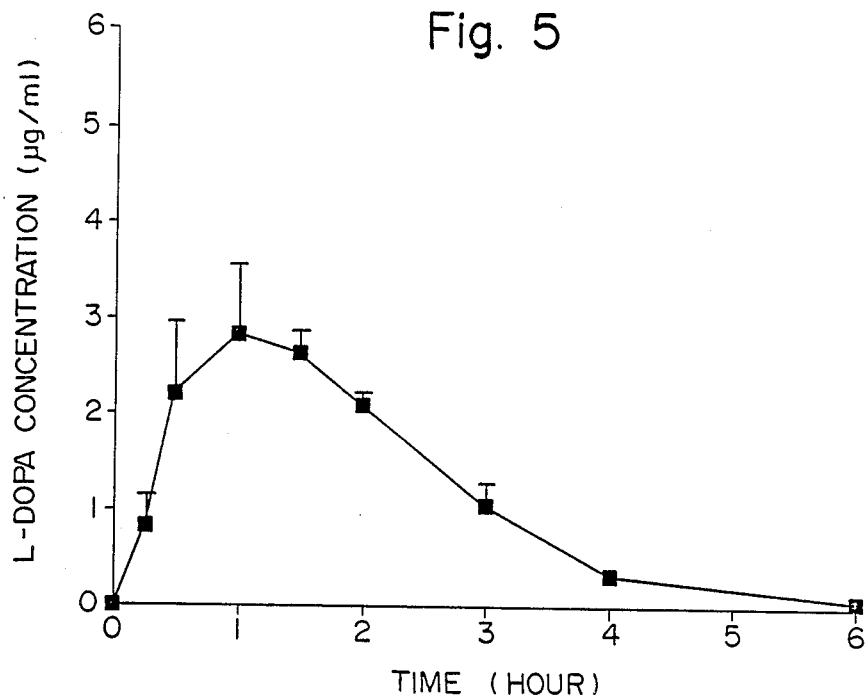
FIG. 5 illustrates change with time of a blood level of L-dopa in orally administering Compound A to Beagle dogs.
Figure 6:
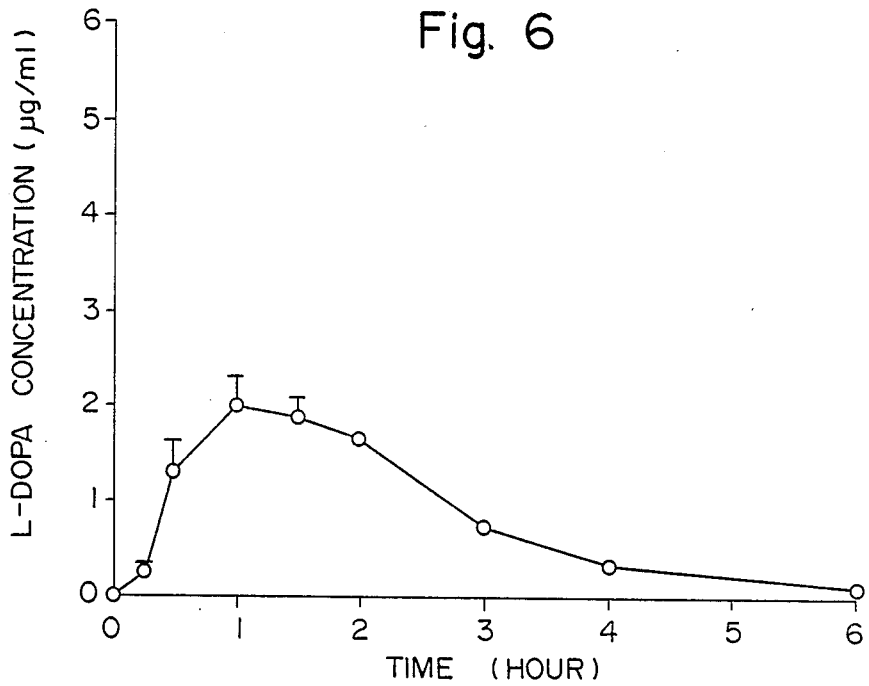
FIG. 6 illustrates change with time of a blood level of L-dopa in orally administering Compound B to Beagle dogs.

The results are shown in FIGS. 4 to 6. In the blood level of L-dopa following oral administration of the test drugs, no rapid increase or elimination is observed and the duration time is markedly prolonged, showing a clinically favorable blood level profile, in comparison with L-dopa as the control drug. Further, in that case, an area under the blood curve (AUC) of the test drugs shows a higher value than that of L-dopa.

TEST EXAMPLE 3

Measuring blood levels of L-dopa after intravenous administration of drugs (rats)

Seven to eight week-old SD-strain male rats (n=3) were previously fasted for 18 hours. Twenty milligrams of L-dopa as a control drug or the equimolar amount of Compound A was dissolved in a concentration of 10 mg/ml in a physiolosical saline containing 50% propylene glycol, and the resulting solution was intravenously administered to the rats at a dose of 10 mg eq./kg, calculated as L-dopa. Immediately after administration, or 5, 15, 30, 45, 60, 90, 120, 150, 180 or 240 minutes after administration, 120 μl of blood was collected through a carotid cannula intubated in advance three days before the test using a heparin-treated glass capillary. The blood was treated as in Test Example 1 and then measured for blood levels of L-dopa.

Figure 7:
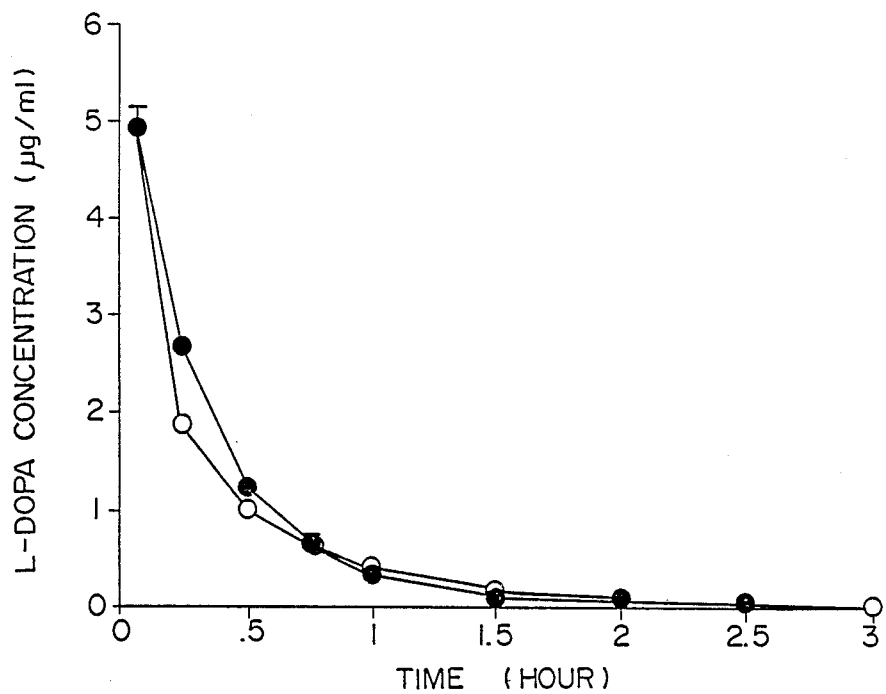
FIG. 7 illustrates change with time of a blood level of L-dopa in intravenously administering Compound A (o) and L-dopa (•) to rats.

The results are shown in FIG. 7. After intravenously administered, Compound A is rapidly and completely hydrolyzed to L-dopa in the systemic circulation. On that occasion, a conversion ratio is estimated to reach about 100%. This means that Compound A possesses high bioavailability and low toxicity, having suitable properties as a prodrug of L-dopa.

TEST EXAMPLE 4

Measuring concentrations of L-dopa in the lumen and tissue of the small intestine by an in situ ligating loop method (rats)

Eight week-old male rats (n=3) were fasted overnight before the test, and then under ether anesthesia, were incised at the abdomen. An acute loop of 8 cm length was ligated in the jejunum. Compound A (1.47 mg) or 1.00 mg of L-dopa as a control drug was suspended in 0.5 ml of 0.5% sodium carboxymethylcellulose together with 0.4 mg of carbidopa, and the suspension was injected into the loop. The loop was returned in the abdominal cabity and the cut portion was then sewn. After a fixed time, the loop was taken out again and the content in the loop was well washed with a ice-cooled physiological saline. The intestinal tissue was homogenated with ethanol containing hydrochloric acid in a 19-fold amount per tissue. The washing liquid and supernatant of the homogenate (3000 rpm, 10 minutes, 4° C.) were properly diluted. In the resulting solutions, the concentration of L-dopa was determined as in Test Example 1 and the concentration of Compound A as follows, respectively. To the solution was added 0.5 volume of an o-phthalaldehyde reagent [prepared by dissolving 8 mg of o-phthalaldehyde and 8 mg of N-acetylcysteine in a mixture of 200 μl of methanol and 800 μl of a 81 mM boric acid buffer solution (pH 8.0)] to give a fluorescent derivative of Compound A. The concentration of Compound A in the samples was measured by HPLC with a fluorescence detector [column: Zorbax $C_8$ (5 μm), 250 mm×4.6 mm φ, mobile phase: methanolcontaining McIlvaine buffer solution, flow rate: 1.0 ml/min., detecting wavelength: exc. 340 nm/emi. 450 nm].

Figure 8:
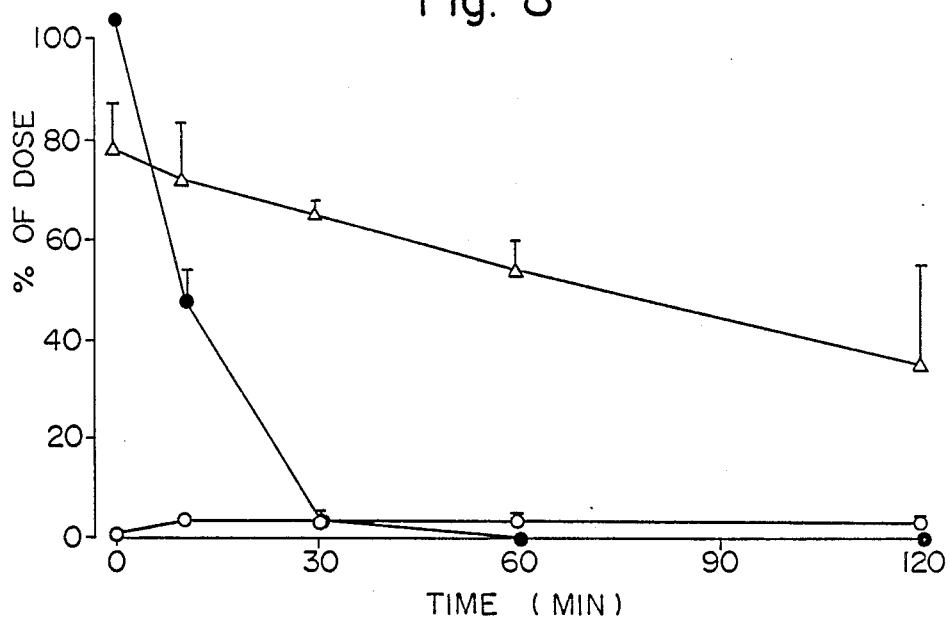
FIG. 8 illustrates change with time of amounts of Compound A (Δ) and L-dopa (o) after injection of Compound A, and amount of L-dopa (•) after injection of L-dopa in the lumen of the small intestine of rats according to an in situ ligating loop method.
Figure 9:
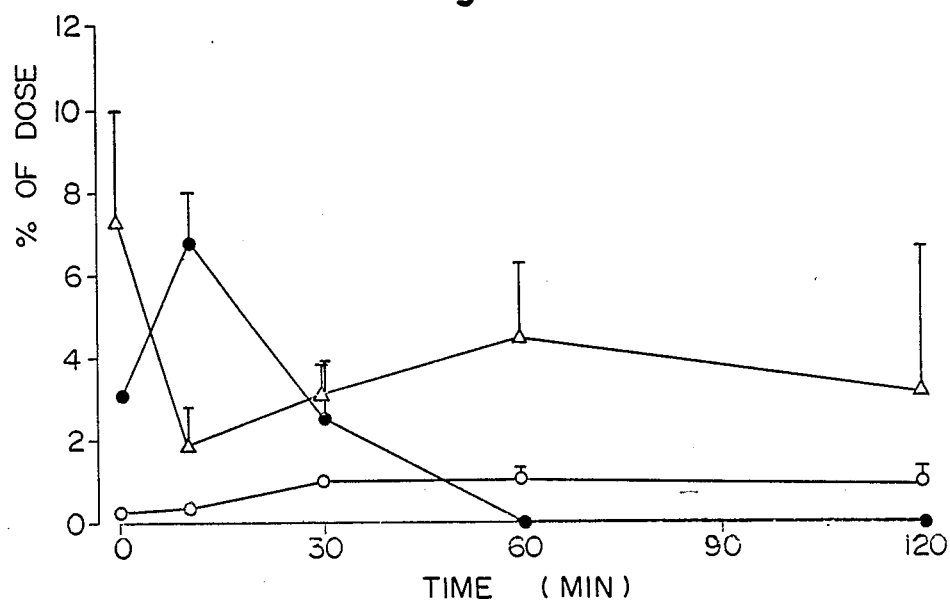
FIG. 9 illustrates change with time of amounts of Compound A (Δ) and L-dopa (o) after injection of Compound A, and amount of L-dopa (•) after injection of L-dopa in the tissue of the small intestine of rats according to an in situ ligating loop method.

The results are shown in FIGS. 8 and 9. The amount of L-dopa in the lumen (washing liquid) and tissue (homogenate) of the small intestine after administration of Compound A was retained for a longer time with less fluctuation than that after administration of L-dopa. Moreover, as the concentration was kept low, it can be expected to decrease gastro-intestinal side effects of a digestive system such as nausea, vomiting, anorexia and ulcer which are problems in clinical application of L-dopa.

TEST EXAMPLE 5

Acute toxicity (1) Oral administration

Each of the test drugs was suspended in a 0.5% sodium carboxymethylcellulose solution containing 0.1% Tween 80 and orally administered to each of ddY-strain male mice (body weight 24 to 31 g, n=5), and a mortality up to 1 week after administration was observed. Toxicity of test compounds (Compounds A and B) was extremely low. The $LD_{50}$ value was 6 g/kg or more in both cases. Where L-dopa as a control drug was orally administered, its $LD_{50}$ value was 3.2 g/kg.

(2) Intraperitoneal administration

Each of the test drugs was suspended in a sterilized physiological saline and intraperitoneally administered to ddY-strain male mice (body weight 24 to 29 g, n=5), and a mortality up to 1 week after administration was observed.

Toxicity of the test compound (Compound A) was very low, and no case of death was observed in the intraperitoneal administration at a dose of 1800 mg/kg either. Where L-dopa as a control drug was intraperitoneally administered at a dose of 1250 mg/kg, the two of five mice were dead. In the intraperitoneal administration of L-dopa at a dose of 1800 mg/kg, all the test mice were dead.

The following examples illustrate this invention more specifically.

EXAMPLE 1

Three grams of L-dopa was suspended in 50 ml of tetrahydrofuran, and 1.5 ml of a 70% perchloric acid aqueous solution was added under stirring with ice cooling at 5° to 10° C. to form a homogeneous solution. To the solution was added dropwise 9.00 ml of pivaloyl chloride, and the reaction was then performed at room temperature for 24 hours. To the reaction mixture was added 200 ml of petroleum ether, and a precipitate was separated by decantation and then dissolved in 100 ml of water. The solution was put on Diaion HP-20 (column capacity about 100 ml), and the column was washed with water until the eluent was neutral. A 40% aqueous methanol was passed to elute the product. The fraction containing the final product was concentrated (about 50 ml), and then left to stand overnight in an ice room. The product was collected by filtration, and recrystallized from 10% aqueous isopropyl alcohol to afford 2.91 g (yield 68%) of 4-pivaloyl-L-dopa (Compound A).

m.p.: 228°–230° C. (decomp.)

IR $v_{max}^{KBr}$(cm$^{-1}$): 3178, 2980, 1743, 1635, 1590, 1521, 1440, 1419, 1302, 1242, 1137

MS (FAB) m/z: 282 [M$^+$+1]

When NMR was measured in methanol containing hydrogen chloride, this compound gave a signal of a single compound. However, when this compound was present in neutral methanol, it was a mixture of 3-(4-hydroxy-3-pivaloyloxy)phenyl-L-alanine and 3-(3-hydroxy-4-pivaloyloxy)phenyl-L-alanine.

NMR (CD$_3$OD) δ: 1.35(9H, s), 2.90+2.91(1H, dd×2, J=14.4 Hz & 8.9 Hz), 3.23+3.26(1H, dd×2, J=14.4 Hz & 4.4 Hz), 3.72+3.73(1H, dd×2, J=8.9 Hz & 4.4 Hz), 6.76+7.03(1H, dd×2, J$^1$=8.3 Hz & 1.9 Hz, J$^2$=7.9 Hz

& 2.2 Hz), 6.89(1H, d×2, J¹=8.3 Hz, J²=9.9 Hz), 6.88+6.90 (1H, d×2, J¹=1.9 Hz, J²=2.2 Hz)

EXAMPLE 2

Using 3.00 g of L-dopa, 1.5 ml of a 70% perchloric acid aqueous solution and 10.0 g of 1-methylcyclopropanecarbonyl chloride as starting materials, the reaction was run at 45° C. for 2 hours. Subsequently, the same treatment as in Example 1 was conducted to obtain 3.00 g (yield 70.7%) of 4-O-(1-methylcyclopropanecarbonyl)-L-dopa (Compound B).

m.p.: 228°-230° C. (decomp.)

IR $\nu_{max}^{KBr}$(cm$^{-1}$): 3178, 2974, 1734, 1635, 1521, 1443, 1419, 1146

MS (FAB) m/z: 280 [M$^+$+1]

NMR (CD$_3$OD) δ: 0.89(2H, dd, J=3.9 Hz & 6.9 Hz), 1.41(3H, s), 1.42(2H, dd. J=3.9 Hz & 6.9 Hz), 3.03+3.05(1H, dd×2, J=14.5 Hz & 8.1 Hz) 3.25+3.27(1H, dd×2, J=5.1 Hz & 13.1 Hz)4.17+4.19(1H, dd×2, J=8.1 Hz & 5.1 Hz), 6.86-6.95Hz(2H, m), 6.77+7.03(1H, dd×2, J¹=2.3 Hz & 8.7 Hz, J²=8.4 Hz & 2.3 Hz)

EXAMPLE 3

Using 1.00 g of L-dopa, 0.5 ml of a 70% perchloric acid aqueous solution and 3.00 g of cyclopropanecarbonyl chloride as starting materials and 20 ml of tetrahydrofuran as a solvent, the reaction was conducted at room temperature for 1 hour. The same treatment as in Example 1 was then conducted to provide 0.46 g (yield 17.0%) of 4-O-cyclopropanecarbonyl-L-dopa (Compound C).

m.p.: 238° to 240° C. (decomp.)

IR $\nu_{max}^{KBr}$(cm$^{-1}$) 3196, 1746, 1662, 1608, 1575, 1443, 1413, 1386, 1354, 1245, 1149

MS (FAB) m/z: 266 M$^+$+1)

NMR (CD$_3$OD/DCl) δ: 1.04-1.10(4H, m), 1.86-1.94 (1H, m), 3.06(1H, dd, J=14.3 Hz & 8.6 Hz), 3.28(1H, dd, J=14.3 Hz & 5.1 Hz), 4.23(1H, dd, J=8.0 Hz & 5.1 Hz), 6.77(1H, dd, J=8.2 Hz & 2.3 Hz), 6.88(1H, dd, J=2.3 Hz), 6.96(1H, d, J=8.2 Hz)

EXAMPLE 4

Using 1.00 g of L-dopa, 0.5 ml of a 70% perchloric acid aqueous solution and 3.00 g of valeryl chloride as starting materials and 20 ml of tetrahydrofuran as a solvent, the reaction was run at 0° C. for 1 hour, and the same treatment as in Example 1 was conducted to form 0.52 g (yield 37.0%) of 4-O-valeryl-L-dopa (Compound D).

m.p.: 226°-228° C. (decomp.)

IR $\nu_{max}^{KBr}$(cm$^{-1}$): 3088, 2968, 1761, 1665, 1575, 1446, 1413, 1356, 1305, 1248, 1149

MS (FAB) m/z: 282 [M$^+$+1]

NMR (CD$_3$OD) δ: 0.96(3H, t, J=7.4 Hz), 1.45+1.46 (2H, sex×2, J=7.4 Hz), 1.70+1.71(2H, q×2, J=7.4 Hz), 2.59+2.60(2H, t×2, J=7.4 Hz), 3.01+3.02(1H, dd×2, J=14.5 Hz & 8.3 Hz), 3.24+3.28(1H, dd×2, J=14.5 Hz & 4.9 Hz), 4.11+4.12 (1H, dd×2, J=8.3 Hz & 4.9 Hz), 6.75+7.02(1H, dd×2, J¹=8.0 Hz & 1.9 Hz, J²=8.2 Hz & 2.0 Hz). 6.86+6.91 (1H, d×2, J=1.9 Hz & 2.0 Hz), 6.93+6.90(1H, d×2, J=8.0 & 8.2 Hz)

EXAMPLE 5

Using 1.00 g of L-dopa, 0.5 ml of a 70% perchloric acid aqueous solution and 3.00 g of 3,3-dimethylbutyryl chloride as a starting material and 30 ml of dioxane as a solvent, the reaction was performed at room temperature for 17 hours. The same treatment as in Example 1 was then conducted to afford 0.23 g (yield 15.6%) of 4-O-(3,3-dimethylbutyryl)-L-dopa (Compound E). m.p.: 255°-258° C. (decomp.)

IR $\nu_{max}^{KBr}$(cm$^{-1}$): 3100, 2962, 1752, 1611, 1521, 1443, 1332, 1296, 1244, 1116, 831

MS (FAB) m/z: 296 [M$^+$+1]

NMR (CD$_3$OD) δ: 1.13+1.14(9H, s×2), 2.47+2.48(2H, s×2), 3.03+3.06(1H, dd×2, J=14.3 Hz & 8.9 Hz), 3.28+3.31(1H, dd×2, J=14.3 Hz & 4.4 Hz), 4.20+4.22(1H, dd×2, J=8.9 Hz & 4.4 Hz), 6.88-6.96(2H, m), 6.77+7.03(1H, dd×2, J¹=8.2 Hz & 2.2 Hz, J²=8.0 Hz & 1.9 Hz)

EXAMPLE 6

Using 1.00 g of L-dopa, 0.5 ml of a 70% perchlorice acid aqueous solution and 5.00 g of octanoyl chloride as starting materials and 30 ml of ethyl acetate as a solvent, the reaction was performed at room temperature for 18 hours. Thereafter, the same treatment as in Example 1 was conducted to obtain 0.50 g (Yield 30.9 %) of 4-O-octanoyl-L-dopa (Compound F). m.p.: 231°-233° C. (decomp.)

IR $\nu_{max}^{KBr}$(cm$^{-1}$): 3124, 2932, 2860, 1761, 1665, 1575, 1413

MS (FAB) m/z: 324 [M$^+$+1]

NMR (CD$_3$OD) δ: 0.95(3H, t, J=7.4 Hz), 1.25-1.50 (8H, m), 1.70(2H, q, J=7.4 Hz), 2.54+2.56(2H, t×2, J=7.4 Hz), 3.12 (1H, dd, J-14.4 Hz & 4.4 Hz), 4.23+4.26(1H, dd×2, J=9.0 Hz & 4.4 Hz), 6.86-6.99(2H, m), 6.80+7.03(1H, dd×2, dd×2, J¹=8.3 Hz & 1.9 Hz, J²=7.9 Hz & 2.1 Hz)

EXAMPLE 7

One gram of L-dopa was suspended in 20 ml of ethyl acetate and 0.5 ml of a 70% perchloric acid aqueous solution was added under stirring with ice cooling at 5° to 10° C. to form a homogeneous solution. To the solution was added dropwise 5.00 g of palmitoyl chloride over a period of 5 minutes. After the additional, the reaction was run at room temperature for 17 hours. To the reaction mixture was added 50 ml of petroleum ether, and the supernatant liquid was removed by decantation. Subsequently, the oily precipitate was washed again with 20 ml of petroleum ether. The precipitate was added to 50 ml of water, and a 1N sodium hydroxide aqueous solution was added under stirring with ice cooling to adjust pH to 5.0 to 5.5. The produce was collected by filtration to give a 1.20 g (yield 54.3%) of 4-O-palmitoyl-Ldopa (Compound G).

m.p.: 218°-220° C. (decomp.)

IR $\nu_{max}^{KBr}$(cm$^{-1}$): 3082, 2926, 1761, 1668, 1578, 1446, 1413, 1356, 1146, 1119

MS (FAB) m/z: 436 [M$^+$+1]

NMR (CD$_3$OD) δ: 0.87(3H, t, J=6.4 Hz), 1.20-1.40 (24H, m), 1.71(2H, q, J=6.7 Hz), 2.58+2.59(2H, t×2, J=6.7 Hz), 3.02-3.13(1H, m), 3.20-3.22(1H, m), 4.10-4.3(1H, m), 6.77+7.30(1H, dd×2, J=8.0 Hz & 2.0 Hz), 6.90-6.96(2H, m)

EXAMPLE 8

The reaction was performed as in Example 7 except using 6.00 g of dodecanoyl chloride instead of palmitoyl chloride in Example 7. There resulted 1.14 g (yield 59.4%) of 4-O-dodecanoyl-L-dopa (Compound H).

m.p.: 231°-232° C. (decomp.)

IR $\nu_{max}^{KBr}$(cm$^{-1}$): 2926, 2854, 1761, 1665, 1578, 1446, 1413, 1119

MS (FAB) m/z: 380 [M++1]

NMR (CD$_3$OD) δ: 0.87(3H, t, J=6.7 Hz), 1.25–1.50 (16H, m), 1.72(2H, q, J=7.3 Hz), 2.59+2.60(2H, t×2, J=7.3 Hz), 3.00–3.10(1H, m), 3.20+3.25(1H, m), 4.18–4.24(1H, m), 6.77+7.03(1H, dd×2, J$^1$=8.0 Hz & 1.9 Hz, J$^2$=8.3 Hz & 2.0 Hz), 6.89–6.93(1H, d×2, J$^1$=2.0 Hz, J$^2$=1.9 Hz), 6.91+6.95(1H, d×2, J$^1$=8.3 Hz, J$^2$=8.0 Hz)

EXAMPLE 9

Using 1.00 g of L-dopa, 0.5 ml of a 70% perchloric acid aqueous solution and 4.0 g of benzoyl chloride as starting materials and 20 ml of tetrahydrofuran as a solvent, the reaction was run at 60° C. for 30 minutes. The same treatment as in Example 1 was then conducted to obtain 4.5 g (yield 30.0%) of 4-O-benzoyl-L-dopa (Compound I).

m.p.: 226°–229° C. (decomp.)

IR $\nu_{max}^{KBr}$(cm$^{-1}$): 3112, 1746, 1647, 1617, 1584, 1314, 1269, 1248, 1059, 708

MS (FAB) m/z: 302 [M++1]

NMR (CD$_3$OD/DCl) δ: 3.13(1H, dd, J=14.3 Hz & 7.8 Hz), 3.35(1H, dd, J=14.3 Hz & 5.4 Hz), 4.26(1H, dd, J=7.8 Hz & 5.4 Hz), 6.83(1H, dd, J=8.5 Hz & 2.0 Hz), 7.05(1H, d, J=8.5 Hz), 7.46–8.21(5H, m)

EXAMPLE 10

The reaction was performed as in Example 9 except using 4.30 g of phenylacetyl chloride instead of benzoyl chloride. There was obtained 0.47 g (yield 29.8 %) of 4-O-phenylacetyl-L-dopa (Compound J).

m.p.: 228°–230° C. (decomp.)

IR $\nu_{max}^{KBr}$(cm$^{-1}$): 3412, 1752, 1665, 1578, 1413, 1245, 1128

MS (FAB) m/z: 316 [M++1]

NMR (CD$_3$OD/DCL) δ: 3.10(1H, dd, J=15.0 Hz & 8.2 Hz), 3.26(1H, dd, J=15.0 Hz & 5.1 Hz), 3.94(2H, s), 4.22(1H, dd, J=8.2 Hz & 5.1 Hz), 6.78(1H, dd, J=8.0 Hz & 1.8 Hz), 6.93(1H, d, J=1.8 Hz), 6.94(1H, d, J=8.0 Hz), 7.27–7.40(5H, m)

EXAMPLE 11

Two grams of L-dopa was dissolved in 6.0 ml of trifluoroacetic acid, and 1.40 ml of pivaloyl chloride was added thereto. The reaction was run at room temperature for 16 hours. Trifluoroacetic acid was evaporated under reduced pressure, and the residue was dissolved in water and treated as in Example 1 to obtain 1.50 g (yield 53.4%) of 4-O-pivaloyl-L-dopa. The spectral data of said compound agree with that of the compound in Example 1.

EXAMPLE 12:

L-dopa perchloroate (3.20 g) was dissolved in 15 ml of tetrahydrofuran, and 1.60 ml of pivaloyl chloride was added thereto. The reaction was performed at 50° to 60° C. for 1 hour. After the reaction was finished, the solvent was evaporated under reduced pressure, and the residue was dissolved in water and treated as in Example 1 to afford 1.40 g (yield 49.8%) of 4-O-pivaloyl-L-dopa. The spectral data of said compound agreed with that of the compound in Example 1.

EXAMPLE 13

N-benzyloxycarbonyl-L-dopa (3.30 g) was dissolved in a mixture of 50 ml of water and 10 ml of ethyl ether. Under stirring with ice cooling, 10 ml of a 1N sodium hydroxide aqueous solution and 10 ml of an ethyl ether solution of 1.20 g pivaloyl chloride were added dropwise at the same time over a period of 30 minutes while keeping pH at 6.0 to 8.0 After the addition was over, the mixture was stirred at room temperature for 1 hour, and diluted with 50 ml of ethyl acetate. Subsequently, 2N hydrochloric acid was added to adjust pH to 2.0. An organic layer was taken out, water-washed and dried over anhydrous magnesium sulfate. After the drying agent was separated by filtration, the solvent was evaporated under reduced pressure. When the residue was purified by silica gel column chromatography (Wakogel C-100, 120 g, eluted with methylene chloride/methanol=5/1), 2.60 g (yield 62.6%) of N-benzyloxycarbonyl-mono-O-pivaloyl-L-dopa was obtained as a pale yellow glass solid.

IR $\nu_{max}^{KBr}$(cm$^{-1}$): 3376, 2980, 1734, 1614, 1344, 1292, 1236, 1059, 738, 699

NMR (CDCl$_3$) δ: 1.35+132(9H, s×2), 2.92–3.12(2H, m), 4.41–4.65(1H, m), 50.1–5.19(2H, m), 5.41(1H, d, J=7.4 Hz), 6.59–7.41(8H, m)

One gram of the above obtained mono-O-pivaloyl product was dissolved in 50 ml of methanol, and the solution was catalytically reduced at a hydrogen pressure of k kg/m$^2$ in the presence of 0.1 g of a 5% palladium/carbon catalyst. After the catalyst was separated by filtration, the solvent was evaporated under reduced pressure. There resulted 0.41 g (reduction yield 60.5%) of 4-O-pivaloyl-L-dopa. The spectral data of said compound completely agreed with that of the compound obtained in Example 1.

EXAMPLE 14

(a) N-benzyloxycarbonyl-L-dopa benzyl ester (852 mg) was dissolved in 20 ml of acetone, and 52 mg of sodium iodide, 254 mg of benzyl chloride and 622 mg of potassium carbonate were added. Subsequently, the mixture was refluxed in an atmosphere of argon for 17 hours with stirring. After the reaction was over, the inorganic salt was removed by filtration. The filtrate was concentrated under reduced pressure, and the residue was purified by liquid chromatography [Lobar column Si 60 (tradename for a product manufactured by Merck), elution solvent: hexane/ethyl acetate=10/1 to 6/1]. There resulted the following two isomers. [The structure of both the isomers were confirmed by O-methylating each of the isomers with methyl iodide and potassium carbonate in acetone, followed by catalystic reduction in methanol in the presence of a 10% palladium/carbon catalyst to form corresponding 4-O-methyl-L-dopa or a 3-O-methyl-L-dopa, and comparing each of the compounds with an authentic sample synthesized separately. (J. Org. Chem., vol. 21, pp. 4696–4698, 1961)]

Two isomers:

N-benzyloxycarbonyl-3-(3-benzyloxy-4-hydroxy)-phenyl-L-alanine benzyl ester

Amount: 354 mg (pale yellow oily product, yield 42%)

IR $\nu_{max}^{neat}$(cm$^{-1}$): 3376, 2926, 1722, 1518, 1458, 1389, 1344, 1275, 1236, 1197, 1122, 1059, 1026, 741, 699

MS (FAB) m/z: 512 [M++1], 378 (base peak)

NMR (CDCl$_3$) δ: 3.04(2H, d, J=6.1 Hz), 4.65–4.68(1H, m), 4.89–5.15(6H, m), 5.22(1H, d, J=8.1 Hz), 5.56(1H, s), 6.52(1 H, dd, J=8.1 Hz & 1.7 Hz), 6.63(1H, d, J=1.7 Hz), 6.77(1H, d, J=8.1 Hz), 7.32–7.40(15H, m)

N-benzyloxycarbonyl-3-(4-benzyloxy-3-hydroxy)phenyl-L-alanine benzyl ester

Amount: 310 mg (pale yellow oily product; yield 36%)

IR $\nu_{max}^{neat}$(cm$^{-1}$): 3412, 3070, 3040, 2744, 1728, 1593, 1515, 1458, 1389, 1341, 1275, 1128, 1059, 1026, 915, 855, 738, 699

MS (FAB) m/z: 512 [M$^+$+1], 167 (base peak)

NMR (CDCl$_3$) δ: 3.01(2H, d, J=5.6 Hz), 4.65(1H, m), 5.04(2H, s), 5.07(2H, s), 5.14(2H, s), 5.22(1H, d, J=8.2 Hz), 5.59(1H, s), 6.46(1H, dd, J=1.9 Hz & 8.1 Hz), 6.66(1 H, d, J=1.9 Hz), 6.73(1H, d, J=8.1 Hz), 7.25–7.40(15H, m)

(b) The 3-benzyloxy product (208 mg) obtained in Example 14-(a) was dissolved in dimethylformamide, and mg of 4-dimethylaminopyridine, 124 mg of triethylamine and 148 mg of pivaloyl chloride were added. The mixture was stirred with heating at 100° C. for 35 minutes. After the reaction was over, ethyl acetate and water were added to the reaction liquid, and the organic layer was washed with a saturated sodium chloride solution. The resulting solution was dried over anhydrous magnesium sulfate, followed by evaporating the solvent. The residue was taken out, purified by thin layer chromatography [Kiesel gel 60F$_{254}$ Art 5744 (Merck), developing solvent: hexane/ethyl acetate=10/3], and recrystallized from a mixture of ethyl ether, isopropyl ether and hexane. There resulted 110 mg (yield 45%) of N-benzyloxy-3-(3-benzyloxy-4-pivaloyloxy)phenyl-L-alanine benzyl ester.

m.p.: 71°–72° C.

IR $\nu_{max}^{KBr}$(cm$^{-1}$): 1755, 1716, 1509, 1461, 1395, 1350, 1287, 1266, 1215, 1188, 1158, 1122, 1056, 1029, 756, 699

MS (EI, high resolution measurement): C$_{36}$H$_{37}$O$_7$N- (found 595,2568/calculated 595,2570)

NMR (CDCl$_3$) δ: 1.24(9H, s), 3.08(2H, d, J=5.3 Hz), 4.68–4.71(1H, m), 4.84(2H, s), 5.05–5.14(4H, m), 5.29(1H, d, J=7.9 Hz), 6.60(1H, dd, J=8.2 Hz & 2.0 Hz), 6.71(1H, m), 6.86(1 H, d, J=8.2 Hz), 7.23–7.37(15H, m)

(c) Using the 4-benzyloxy product obtained in Example 14-(a) as a starting material, the reaction was performed as in (b) above. There resulted N-benzyloxy-3-(4-benzyloxy-3-pivaloyloxy)phenyl-L-alanine benzyl ester as a colorless oily product.

IR $\nu_{max}^{neat}$(cm$^{-1}$): 2974, 1752, 1515, 1458, 1389, 1344, 1266, 1215, 1122, 1059, 1026, 741, 696

MS (EI, high resolution measurement): C$_{36}$H$_{37}$O$_7$N (found 595,2577/calculated 595,2570)

NMR (CDCl$_3$) δ: 1.24(9H, s), 3.03(2H, d, J=5.7 Hz), 4.65–4.67(1H, m), 4.97(2H, s), 5.09(2H, s), 5.11(2H, s), 5.32(1 H, d, J=8.0 Hz), 6.79–6.80(3H, m), 7.23–7.39(15H, m)

(d) The 4-pivaloyloxy product (99 mg) obtained in (b) of Example 14 was dissolved in a mixture of 223 l of a 15% hydrogen chloride-methanol solution and 6 ml of methanol, and catalytically reduced at a hydrogen pressure of 4 kg/m$^2$ for 6 hours in the presence of 367 mg of a palladium/carbon catalyst. After the reduction was finished, the catalyst was separated by filtration, and the filtrate was dried under reduced pressure and then treated with ethyl ether to afford 30 mg (yield 64%) of 4-O-pivaloyl-L-dopa hydrochloride.

m.p.: 170°–173° C. (decomp.)

IR $\nu_{max}^{KBr}$(cm$^{-1}$): 3424, 2980, 1737, 1611, 1524, 1485, 1440, 1404, 1371, 1296, 1236, 1131

NMR (CD$_3$OD/DCl) δ: 1.35(9H, s), 3.06(1H, dd, J=14.5 Hz & 7.9 Hz), 3.28(1H, dd, J=14.5 Hz & 5.2 Hz), 4.23(1H, dd, J=7.9 Hz & 5.2 Hz), 6.78(1H, dd, J=8.2 Hz & 2.2 Hz), 6.90(1H, d, J=2.2 Hz), 6.92(1H, d, J=8.2 Hz)

(e) Using the 3-pivaloyloxy product obtained in (c) of Example 14 as a starting material, the reaction was run as in (d) of Example 14. There was obtained 3-O-pivaloyl-L-dopa hydrochloride.

m.p.: 140°–145° C. (decomp.)

IR $\nu_{max}^{KBr}$(cm$^{-1}$): 2980, 1740, 1626, 1524, 1488, 1449, 1401, 1371, 1293, 1251, 1203, 1137

NMR (CD$_3$OD/DCl) δ: 1.36(9H, s), 3.08(1H, dd, J=14.8 Hz & 7.6 Hz), 3.26(1H, dd, J=14.8 Hz & 4.9 Hz), 4.22(1H, dd, J=7.6 Hz & 4.9 Hz), 6.92(1H, d, J=1.9 Hz), 6.94(1H, d, J=8.5 Hz), 7.04(1H, dd, J=8.5 Hz & 1.9 Hz)

EXAMPLE 15

To a mixed powder comprising 147 parts of 4-O-pivaloyl-L-dopa, 10 parts of carbidopa, 35 parts of lactose, 13.5 parts of corn starch and 12 parts of calcium carboxymethylcellulose was added a kneading solution composed of 6 parts of methyl cellulose and a suitable amount of water, and they were kneaded, pulverized and dried. Subsequently, 1.5 parts of magnesium stearate was added, and they were mixed to produce a tablet (225 mg).

EXAMPLE 16

A tablet (225 mg) was produced as in Example 15 using 147 parts of 4-0-pivaloyl-L-dopa, 25 parts of carbidopa, 27 parts of sucrose, 9.5 parts of corn starch, 9 parts of calcium carboxymethylcellulose, 6 parts of methyl cellulose and 1.5 parts of magnesium stearate.

EXAMPLE 17

4-O-pivaloyl-L-dopa (442 parts), 45 parts of corn starch, 40 parts of crystalline cellulose and 20 parts of carboxymethyl cellulose were mixed, and 3 parts of magnesium stearate was further added. After they were mixed, a tablet (550 mg) was produced by direct compression.

EXAMPLE 18

4-O-pivaloyl-L-dopa (147 mg), 32 mg of corn starch, 25 mg of carbidopa, 43 mg of lactose and 2 mg of magnesium stearate were mixed, and the mixture was filled in a capsule.

An activity of L-dopa against Parkinson's disease is generally known to be correlated to a blood level of L-dopa, and the- drugs of this invention bring forth clinically favorable pharmacokinetic profile of L-dopa. That is, the drugs of this invention, after administration, keep a clinically effective blood level of L-dopa for a long period of time without abrupt increase or rapid elimination of blood level of L-dopa. Further, bioavailability of the drugs in this invention is good, and it is also possible to decrease the dose as a prodrug, calculated as L-dopa being its parent compound. Still further, as the drugs of this invention have very low toxicity, they are extremely useful for the medical treatment of the Parkinson's disease against which patients have to take medicines for a long period of time.

What is claimed is:

1. An L-dopa derivative represented by formula [I]

1.

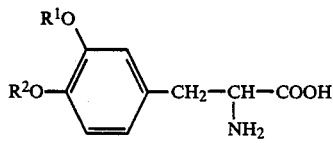

wherein one of $R^1$ and $R^2$ denotes a hydrogen atom and the other denotes a group of the formula R—CO— in which R denotes a linear or branched $C_1$-$C_{19}$ alkyl, $C_2$-$C_{19}$ alkenyl, $C_3$-$C_7$ cycloalkyl, phenyl, $C_7$-$C_{12}$ aralkyl, $C_1$-$C_6$ alkoxy or $C_7$-$C_{12}$ aralkyloxy group, provided that said cycloalkyl, phenyl, aralkyl or aralkyloxy group may have one or two substituents selected from the group consisting of $C_1$-$C_4$ alkyl, $C_1$-$C_4$ alkoxy and halogen; or a pharmaceutically acceptable acid addition salt thereof.

2. The L-dopa derivative or its acid addition salt of claim 1 which is represented by formula [1-a]

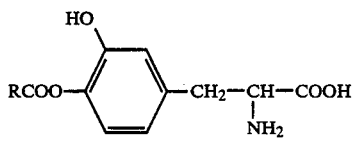

wherein R is as defined in claim 1,

3. The L-dopa derivative or its acid addition salt of claim 1 wherein R is a branched $C_3$-$C_5$ alkyl or linear $C_4$-$C_{15}$ alkyl group, or a $C_3$-$C_6$ cycloalkyl group which may be substituted with one or two $C_1$-$C_4$ alkyl groups.

4. The L-dopa derivative or its acid addition salt of claim 1 wherein R is a branched $C_3$-$C_5$ alkyl group or a $C_3$-$C_6$ cycloalkyl group which may be substituted by one $C_1$-$C_4$ alkyl group.

5. The L-dopa derivative or its acid addition salt of claim 4 wherein R is a tert-butyl, cyclopropyl or 1-methylcyclopropyl group.

6. The L-dopa derivative or its acid addition salt of claim 5 wherein R is a tert-butyl group.

7. The L-dopa derivative or its acid addition salt of claim 1 which are 3-(3-hydroxy-4-pivaloyloxy)phenyl-L-alanine, 3-(3-hydroxy-4-cyclopropanecarbonyloxy)-phenyl-L-analine, 3-{3-hydroxy-4-(1-methylcyclopropanecarbonyl)oxyl}phenyl-L-alanine or their acid addition salts.

8. A pharmaceutical composition for treating Parkinson's disease comprising an anti-Parkinsonism's effective amount of an L-dopa derivative represented by the formula [I]

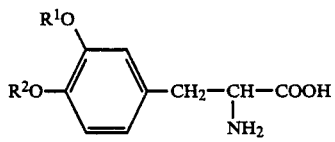

wherein one of $R^1$ and $R^2$ denotes a hydrogen atom and the other denotes a group of the formula R—CO— in which R denotes a linear or branched $C_1$-$C_{19}$ alkyl, $C_2$-$C_{19}$ alkenyl, $C_3$-$C_7$ cycloalkyl, phenyl, $C_7$-$C_{12}$ aralkyl, $C_1$-$C_6$ alkoxy or $C_7$-$C_{12}$ aralkyloxy group, provided that said cycloalkyl, phenyl, aralkyl or aralkyloxy group may have one or two substituents selected from the group consisting of $C_1$-$C_4$ alkyl, $C_1$-$C_4$ alkoxy and halogen, or a pharmaceutically acceptable acid addition salt thereof; and a pharmaceutically acceptable carrier or diluent.

9. The pharmaceutical composition of claim 8 further comprising an L-aromatic amino acid decarboxylase inhibitor selected from the group consisting of (−)-L-alpha-hydrazino-3,4-dihydroxy-alpha-methyl-hydrocinnamic acid and DL-serine-2((2,3,4-trihydroxyphenyl)methyl)hydrazide.

10. The pharmaceutical composition of claim 9 wherein the molar ratio of said L-dopa derivative or its pharmaceutically acceptable acid addition salt to said L-aromatic amino acid decarboxylase inhibitor is within the range of 1:1 to 15:1.

11. The pharmaceutical composition of claim 8 wherein said L-dopa derivative is represented by the formula [Ia]

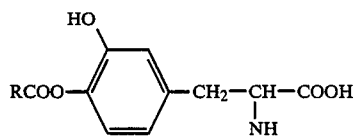

12. The pharmaceutical composition of claim 8, wherein R is a branched $C_3$-$C_5$ alkyl or linear $C_4$-$C_{15}$ alkyl group, or a $C_3$-$C_6$ cycloalkyl group which may be substituted with one or two $C_1$-$C_4$ alkyl groups.

13. The pharmaceutical composition of claim 8, wherein R is a branched $C_3$-$C_5$ alkyl group or a $C_3$-$C_6$ cycloalkyl group which may be substituted by one $C_1$-$C_4$ alkyl group.

14. The pharmaceutical composition of claim 13, wherein R is a tert-butyl, cyclopropyl or 1-methylcyclopropyl group.

15. The pharmaceutical composition of claim 14, wherein R is a tert-butyl group.

16. The pharmaceutical composition of claim 8, wherein said L-dopa derivative is selected from the group consisting of 3-(3-hydroxy-4-pivaloyloxy)phenyl-L-alanine, 3-(3-hydroxy-4-cyclopropanecarbonyloxy)-phenyl-L-alanine, 3-(3-hydroxy-4-(1-methylcyclopropanecarbonyloxy)phenyl-L-alanine and pharmaceutically acceptable acid addition salts thereof.

17. A method for treating a patient of Parkinson's disease comprising orally administering an anti-Parkinsonism's effective amount of an L-dopa derivative represented by the formula [I]

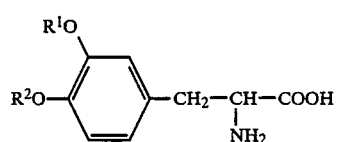

wherein one of $R^1$ and $R^2$ denotes a hydrogen atom and the other denotes a group of the formula R—CO— in which R denotes a linear or branched $C_1$-$C_{19}$ alkyl, $C_2$-$C_{19}$ alkenyl, $C_3$-$C_7$ cycloalkyl, phenyl, $C_7$-$C_{12}$ aralkyl, $C_1$-$C_6$ alkoxy or $C_7$-$C_{12}$ aralkyloxy group, provided that said cycloalkyl, phenyl, aralkyl or aralkyloxy group may have one or two substituents selected from the group consisting of $C_1$-$C_4$ alkyl, $C_1$-$C_4$ alkoxy and halogen, or a pharmaceutically acceptable acid addition salt thereof to said patient.

18. The method of claim 17, wherein said L-dopa derivative or its pharmaceutically acceptable acid addition salt is orally administered to said patient together with an L-aromatic acid decarboxylate inhibitor selected from the group consisting of (—)-L-alpha-hydrazino-3,4-dihydroxy-alphamethyl-hydrocinnamic acid and DL-serine-2-((2,3,4-trihydroxyphenyl)methyl) hydrazide.

19. The method of claim 18, wherein the molar ratio of said L-dopa derivative or its pharmaceutically acceptable acid addition salt to said L-aromatic amino acid decarboxylase inhibitor is within the range of 1:1 to 15:1.

20. The method of claim 17, wherein said L-dopa derivative is represented by the formula [Ia]

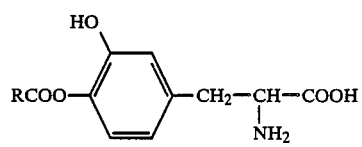

wherein R is as defined in claim 17.

21. The method of claim 17, wherein R is a branched $C_3$–$C_5$ alkyl or linear $C_4$–$C_{15}$ alkyl group, or a $C_3$–$C_6$ cycloalkyl group which may be substituted with one or two $C_1$–$C_4$ alkyl groups.

22. The method of claim 17, wherein R is a branched $C_3$–$C_5$ alkyl group or a $C_3$–$C_6$ cycloalkyl group which may be substituted by one $C_1$–$C_4$ alkyl group.

23. The method of claim 22, wherein R is tert-butyl, cyclopropyl or 1-methylcyclopropyl group.

24. The method of claim 23, wherein R is a tert-butyl group.

25. The method of claim 17, wherein said L-dopa derivative is selected from the group consisting of 3-(3-hydroxy-4-pivaloyloxy)phenyl-L-alanine, 3-(3-hydroxy-4-cyclopropanecarbonyloxy)-phenyl-L-alanine, 3-(3-hydroxy-4-(1-methylcyclopropanecarbonyloxy)phenyl-L-alanine and pharmaceutically acceptable acid addition salts thereof.

* * * * *